United States Patent [19]

Palmer

[11] Patent Number: 5,608,197
[45] Date of Patent: Mar. 4, 1997

[54] MOLECULAR PROCESSES AND APPARATUS

[75] Inventor: Richard E. Palmer, Birmingham, United Kingdom

[73] Assignee: The BOC Group plc, Windlesham, United Kingdom

[21] Appl. No.: 289,151

[22] Filed: Aug. 11, 1994

[30] Foreign Application Priority Data

Aug. 15, 1993 [GB] United Kingdom .................. 9317256

[51] Int. Cl.$^6$ ............................................. C07B 61/00
[52] U.S. Cl. .............................. 204/157.15; 204/157.44; 204/157.63; 204/164
[58] Field of Search ................... 204/157.15, 157.44, 204/157.63, 164

[56] References Cited

U.S. PATENT DOCUMENTS

| | | | |
|---|---|---|---|
| 4,195,606 | 4/1980 | Wallis, Jr. et al. | 123/119 E |
| 5,059,292 | 10/1991 | Collins et al. | 204/164 |
| 5,201,681 | 4/1993 | Okunuki et al. | 445/24 |

Primary Examiner—Elizabeth C. Weimar
Assistant Examiner—C. Delacroix-Muirheid
Attorney, Agent, or Firm—David M. Rosenblum; Larry R. Cassett

[57] ABSTRACT

A method for effecting the initiation of a molecular process or reaction in a substance, which comprises bringing the substance into contact with a surface of a cold cathode device and applying an electric potential across the cold cathode device to cause electrons to be emitted from the surface thereof with an energy level sufficient to effect the initiation.

7 Claims, 3 Drawing Sheets

MOLECULAR PROCESSES AND APPARATUS

BACKGROUND OF THE INVENTION

This invention relates to a method and apparatus for effecting the initiation of molecular processes in substances present on the surface of the apparatus.

The initiation or catalysis of molecular processes or reactions can be conducted by a variety of means and many ways of effecting them are known.

The present invention is concerned with the provision of a novel means of effecting the initiation and/or catalysis of molecular processes by means of the bombardment of molecules by electrons emitted from a particular type of source, which means it allows for good control of the energy of the electrons during the bombardment.

SUMMARY OF THE INVENTION

In accordance with the invention, there is provided a method for effecting the initiation of a molecular process or reaction in a substance, which comprises bringing the substance into contact with a surface of a cold cathode device and applying an electric potential across the cold cathode device to cause electrons to be emitted from the surface thereof with an energy level sufficient to effect the initiation.

The term "cold cathode" is well known in the electronics art and can be simply defined as a device incorporating an electrode from which electron emission is caused by a high potential gradient across the cold cathode device at normal temperatures, for example, those less than 100° C. and commonly ambient temperatures.

Examples of cold cathodes are:

i) "Tip emitters"—which are generally made from a number of silicon or tungsten cones.

ii) "Back-biassed junction cold cathodes"—in which electrons are accelerated across a p-n junction near its surface and emitted into vacuum allowing high electron emission densities.

iii) "metal-insulator-metal (MIM) devices"—in which a thin sandwich of an insulating material layer is prepared between two metal layers of the same or different metals.

Cold cathodes generally, and in particular each of the above types of cold cathode device can be operated through the application of, and control of, a voltage across the devices. Control of the voltage is critical to ensure that electrons emitted from the device have the correct level of kinetic energy in particular to effect initiation of the desired molecular process in the substance in contact with the device.

Although each of the above types of cold cathode may be employed in the method of the invention, it has been found that MIM cold cathode devices in particular can be used to good effect.

As stated above, such MIM devices comprise a metal-insulator-metal sandwich in which each metal layer may be of the same or different metal. With a sufficient electric potential (voltage) applied across the device, i.e. one metal layer being biassed positively and the other negatively with respect to each other, electrons are emitted from the positively biassed metal layer.

As long as the negatively biassed layer is made of a relatively good conductor, its composition is not particularly critical. Of greater importance is the selection of the positively biassed layer for which gold, silver, copper, tin, bismuth, cobalt, iron, iridium, nickel, lead and platinum can be employed; most preferably the metal employed for this layer is one of the first four of the above list. Other metals which might be employed include aluminum, beryllium, chromium, magnesium, manganese and zinc. Carbon and silicon are also candidates for the positively biassed layer and these elements would be included in the term "metal" for the purposes of this specification.

It has been found that the cleanliness of the metal-insulator-metal layer interfaces is crucial for stable electron emission from the device.

In preferred embodiments, the MIM devices operate in practice with an electric potential between the metal layers leading to electron transport from the negatively biassed layer to the positively biassed layer—the device "current" (and thereafter emission from the device) through metallic microfilaments which grow in situ through the insulating layer. The process by which these microfilaments are made is sometimes referred to as "electro-forming" or simply "forming" and occurs in the MIM device once a threshold voltage across the device is exceeded.

Despite the electro-forming process occurring in preferred MIM devices, the current emitted by the MIM when sufficiently high voltages are applied across the device appears to include a contribution from direct field emission of electrons involving quantum mechanical tunnelling through the device from the negatively biassed metal layer.

The choice of insulator layer thickness is therefore crucial to successful operation of the device; in particular, it must be sufficiently thin that the device current is large enough yet thick enough to prevent dielectric breakdown when the voltages required across the device for electron emission are applied.

Generally an insulator layer thickness of from 100 to 1,000 angstroms (Å) has been found to be useful. Preferably the thickness is at least 200 Å, for example 300 Å.

The thickness of the metal layers is not so critical. In general, however, the negatively biassed layer can be as thick as required to conduct the necessary current whereas the positively biassed layer should ideally be as thin as possible to provide maximum electron emission from the device.

A very thin metal layer may nevertheless be associated with a relatively high electrical resistance and it is expedient to ensure that the resistance of the positively biassed layer, and preferably the other layer also, is sufficiently low, for example less than 40 ohms. This commonly is associated with a metal layer thickness of about 500 to 2,000 Å, for example about 1,000 Å.

In use of cold cathode methods of the invention, molecules to be the subject of the molecular process can be adsorbed on to a sufficiently cold cathode surface, for example at or (normally) below ambient temperatures that it produces a condensed layer of molecules, the thickness of which is controlled by the amount of gas (i.e. based on the pressure and dosing time) allowed in to the chamber. The molecular process can then proceed when the cathode voltage is turned on.

Alternatively, the method may involve a flow (or pulses) of gas molecules to be the subject of the molecular process across the surface of the cold cathode device while it is subject to, for example, ambient temperature.

The pressures at which the chamber in which the molecular processes can be conducted may vary depending on a number of factors. For example, in the first mode of operation above with condensation of molecules on the surface of the device, the process is largely unaffected by pressure overall. The pressure can generally be relatively low with gas being pumped from the chamber during the process. It is possible, however, for the processes to be operated at pressure approaching ambient pressure.

Equally, in the second mode of operation above with a flow of gas molecules across the surface of the device, a pressure range of between $5\times10^{-9}$ mbar (the base pressure used) and $5\times10^{-6}$ mbar (the maximum pressure for satisfactory use of a mass spectrometer to detect reaction ion products), has been found to be useful; the yield varied linearly with dosing pressure indicating that the yield is limited by the number of gas molecules striking the surface of the cathode device.

Equally, the voltage applied across the cold cathode will vary depending on the molecular process to be initiated by the method of the invention. The following table lists some typical gas-phase resonance energies for the production of the stated ion from its molecule.

TABLE

| Ion/molecule | Resonance energies (eV) |
| --- | --- |
| $Cl^-/CCl_4, CHCl_3$ | 0.0–0.2 |
| $F^-/F_2$ | 0.09 |
| $Cl^-/Cl_2$ | 0.03; 2.5; 9.7 |
| $Br^-/Br_2$ | 0.07; 0.5; 1.4; 3.7; 5.3; 8.5 |
| $I^-/I_2$ | 0.05; 0.9; 2.5 |
| $H^-/H_2$ | 3.75; 10.2; 13.9 |
| $Cl^-/HCl$ | 0.81; 0.84 |
| $Br^-/HBr$ | 0.28 |
| $I^-/HI$ | 0.0 |
| $H^-/HCl$ | 6.9; 9.2 |
| $H^-/H_2O$ | 6.5; 8.6 |
| $OH^-/H_2O$ | 6.4; 8.4; 11.2 |
| $HS^-/H_2S$ | 2.3 |
| $H^-/H_2S$ | 5.5; 8.0 |
| $S^-/H_2S$ | 10.0 |
| $O^-/O_2$ | 6.5 |
| $O^-/CO_2$ | 4.4; 8.0 |
| $O^-/NO$ | 8.0 |
| $O^-/CO$ | 9.8, 11.0 |

It should be noted that there is considerable structure in the ion yield spectra as a function of electron energy so that more than one "peak" may be observed.

The process of the invention is in general highly tunable and the energy of electrons emitted by the cold cathode may be chosen to populate the resonance level (negative ion state) of one type of molecule present, i.e. adsorbed, on the surface rather than another type; another choice of electron energy can select another species. The key to the principle of operation of the method of the invention is that electrons are emitted from that surface of the cold cathode onto which the reactant molecules are in contact and adsorbed. The method can therefore operate in a relatively high pressure stream of reactant gas flow.

BRIEF DESCRIPTION OF THE DRAWINGS

For a better understanding of the invention, reference will now be made for the purposes of exemplification only, to the accompanying drawings, in which.

DETAILED DESCRIPTION

Figure 1:
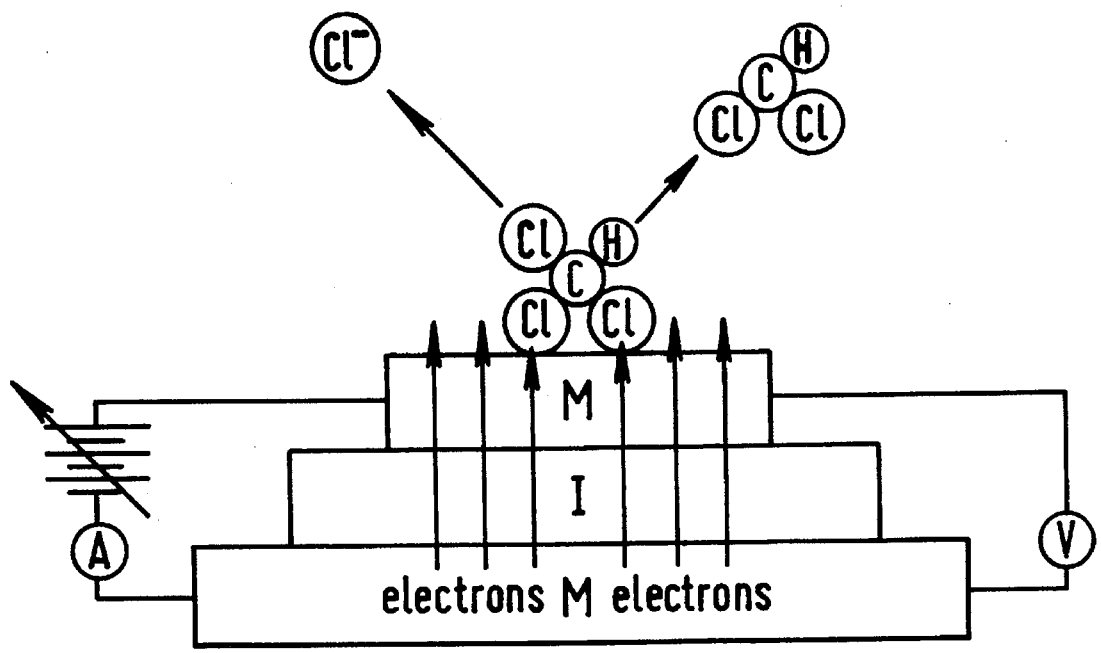
FIG. 1 is a schematic representation of a cold cathode device for use in the method of the invention.

With reference to the drawings, FIG. 1 shows a microelectronic device for use to initiate and control a chemical reaction. It comprises a thin film metal-insulator-metal (MIM) sandwich in which the metal layers are both copper and the insulating layer is $SiO_x$. All the layers were produced by evaporation from resistively heated boats in ultra-high vacuum.

The cold cathode device shown in FIG. 1 was employed to initiate a molecular reaction with chloroform ($CCl_3H$) in a reactor chamber. The chloroform was introduced into the chamber so that chloroform molecules were adsorbed onto the outer (top) surface of the device and the electron energy of the device was set (by controlling the voltage applied across the device with the positively biassed metal layer at the top) to correspond to a dissociative electron attachment (DA) resonance in the adsorbate, thereby effecting molecular dissociation represented by:

The cross section for this process shows well defined resonances at specific energies corresponding to affinity levels of the target molecule into which the incident electron is injected.

Figure 2:
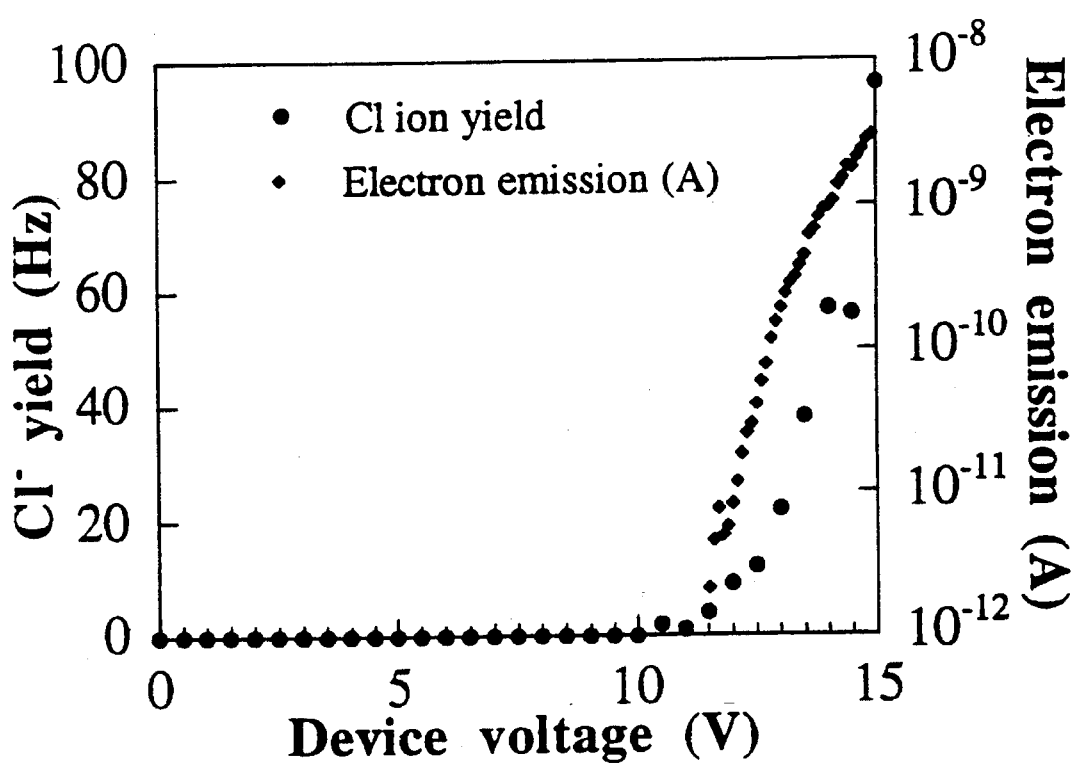
FIG. 2 is a graph of the yield of $Cl^-$ ions desorbed from the outer surface of a cold cathode (MIM) device, on which chloroform is adsorbed, as a function of the voltage applied across the device.

FIG. 2 shows the yield of $Cl^-$ ions desorbed from the outer surface of a metal-insulator-metal (MIM) device on which chloroform, $CCl_3H$, is adsorbed by exposing the device to a pressure of $10^{-8}$ mbar of $CCl_3H$ gas admitted to the vacuum chamber housing the device for fifty seconds (an exposure of 0.5 Languirs), as a function of the voltage applied across the device. The desorbed ions are detected with a pulse counting mass spectrometer. Also plotted is the current of electrons emitted from the device. It is evident from FIG. 2:

(a) that the weakly adsorbed $CCl_3H$ is dissociated by the device, and (b) that dissociation arises from the emission of electrons from the device, as witnessed by the similar voltage thresholds for electron emission and ion desorption. Since the voltage is set via a computer interface, this is in effect a "voltage-controlled catalyst" programmed by a computer.

Figure 3:
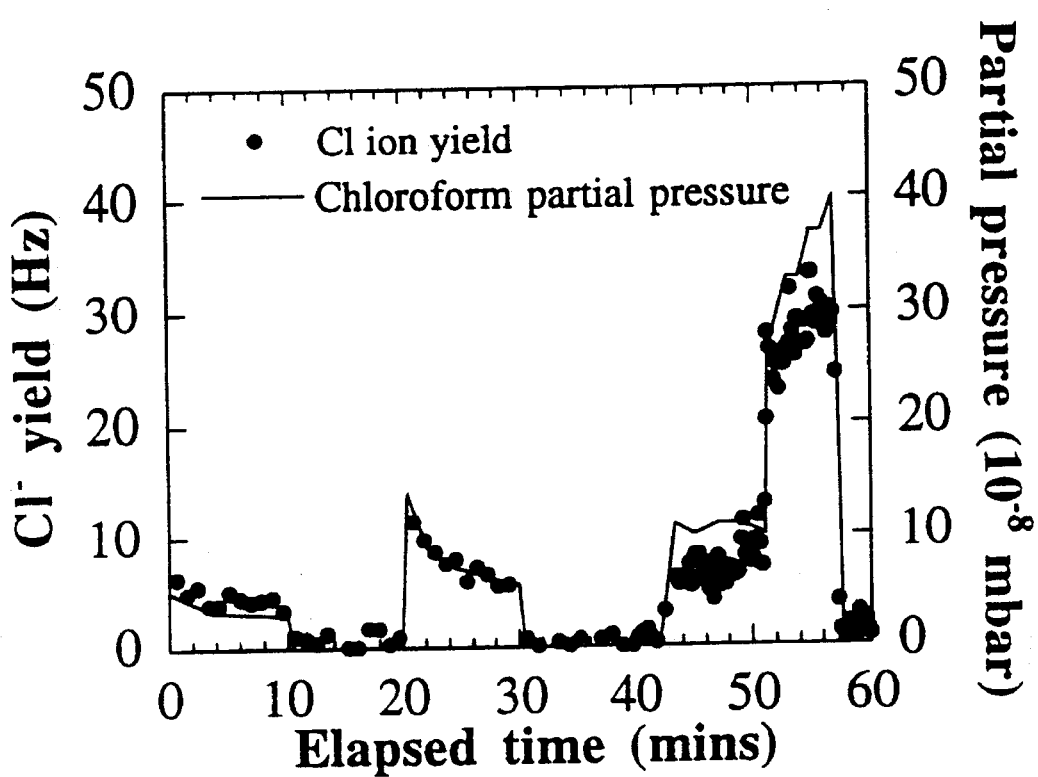
FIG. 3 shows, separately from the example of FIG. 2, a graph of the desorbed $Cl^-$ signal from a chloroform source signal recorded as a function of time while the device is exposed to pulses of $CCl_3H$ gas.

FIG. 3 gives another example of the device in operation; here pulses of $CCl_3H$ gas are let into the vacuum chamber housing the device, and the desorbed $Cl^-$ signal is recorded as a function of time while the device is running under steady operating conditions. The molecular dissociation signal clearly tracks the admitted gas pressure, showing that under these conditions the operation of the device is gas flux limited rather than emission current limited.

I claim:

1. A method for effecting the initiation of a molecular process or reaction in a substance having a dissociative electron attachment resonance, said method comprising bringing the substance into contact with a surface of a cold cathode device from which electrons are emitted so that the substance is adsorbed on said surface and applying an electric potential across the cold cathode device to cause said electrons to be emitted from the surface on which the substance is adsorbed with an energy level sufficient to effect the initiation of said molecular process or reaction.

2. The method according to claim 1 in which the cold cathode is a metal-insulatormetal (MIM) device.

3. The method according to claim 2 in which the insulator layer of the MIM device has a thickness of from 100 to 1000 angstroms.

4. The method according to claim 3 in which the insulator layer of the MIM device has a thickness of at least 200 angstroms.

5. The method according to claim 1 in which the electrical resistance of the positively biased layer is less than 40 ohms.

6. The method according to claim 1 in which the metal layers of the MIM device are both copper and the insulating layer is a silicon oxide ($SiO_x$).

7. The method according to claim 1 which initiates a molecular reaction with chloroform ($CCl_3H$).

* * * * *